United States Patent [19]

Driscoll et al.

[11] Patent Number: 4,692,547

[45] Date of Patent: Sep. 8, 1987

[54] PROCESS FOR THE PREPARATION OF GLYOXYLIC HEMIACETAL ESTERS

[75] Inventors: Robert K. Driscoll, Frankfurt am Main; Ernst I. Leupold, Neu-Anspach; Wolfgang Ebertz, Bonn, all of Fed. Rep. of Germany

[73] Assignee: Hoechst Aktiengesellschaft, Frankfurt am Main, Fed. Rep. of Germany

[21] Appl. No.: 810,519

[22] Filed: Dec. 18, 1985

[30] Foreign Application Priority Data

Dec. 20, 1984 [DE] Fed. Rep. of Germany ....... 3446528

[51] Int. Cl.4 .............................................. C07C 67/31
[52] U.S. Cl. .................................... 560/186; 560/179; 562/587
[58] Field of Search ................................ 560/179, 186

[56] References Cited

U.S. PATENT DOCUMENTS 4,156,093  5/1979  Christidis ............................ 560/186

Primary Examiner—Werren B. Lone
Assistant Examiner—Vera C. Clarke
Attorney, Agent, or Firm—Curtis, Morris & Safford

[57] ABSTRACT

The invention relates to a process for the preparation of glyoxylic hemiacetal esters, in which first glycolic esters are oxydehydrogenated to give glyoxylic esters, and then the latter are reacted with an alcohol. The gaseous reaction mixture formed in the oxydehydrogenation is introduced, together with an excess of an alcohol which is suitable as an entraining agent, into a distillation column and then the water of reaction is distilled overhead together with other low-boilers and part of the excess alcohol, the glyoxylic hemiacetal ester and the remainder of the excess alcohol resulting as the bottom product.

In a variant of the process, use is made of an additional inert entraining agent whose azeotrope with water boils below 90° C. and below the alcohol which is used, and then the water of reaction is distilled overhead with the assistance of this entraining agent.

8 Claims, No Drawings

PROCESS FOR THE PREPARATION OF GLYOXYLIC HEMIACETAL ESTERS

The present invention relates to a process for the preparation of glyoxylic hemiacetal esters from glycolic esters.

It is disclosed in U.S. Pat. No. 4,340,748 that glycolic esters can be oxydehydrogenated on heterogeneous catalysts in the gas phase to give glyoxylic esters. The discharge from the reactor essentially contains glyoxylic ester, water, unreacted glycolic ester and small amounts of the alcohol derived from the ester group. The condensation of gas mixtures of this type results in mixtures, which are difficult to fractionate, of hydrates, hemiacetals and acetals of the glyoxylic ester and glyoxylic acid.

A method is proposed, in German Patent Application No. P 33 23 372.1, for the preparation of a glyoxylic ester, in which the undesired formation of the secondary products glyoxylic ester hydrates, glyoxylic hemiacetal esters, glyoxylic acetal esters and glyoxylic acid is prevented when, before the start of condensation, the water and the alcohol which has been produced as a by-product are removed with an entraining agent from the gaseous product mixture. The formation of a hemiacetal ester is substantially suppressed in this manner.

In contrast, the object of the present invention is not to prevent the formation of the hemiacetal ester but to prepare it.

The present invention thus relates to a process for the preparation of glyoxylic hemiacetal esters, which comprises catalytic oxydehydrogenation of glycolic esters in the gas phase to give glyoxylic esters and then reaction of the latter with an alcohol, the gaseous reaction mixture formed in the oxydehydrogenation being introduced together with an excess of an alcohol which is suitable as an entraining agent into a distillation column, and then the water of reaction being distilled overhead with other low-boilers and part of the excess alcohol, the glyoxylic hemiacetal ester and the remainder of the excess alcohol resulting as the bottom product. Thus, first the glycolic ester is catalytically oxydehydrogenated in the gas phase to give glyoxylic esters, and the latter are then reacted with alcohols to give the corresponding hemiacetal esters:

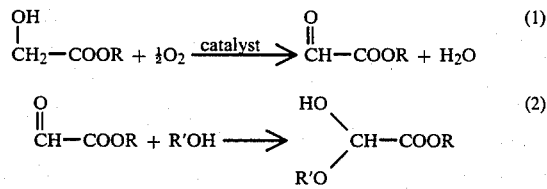

In the first stage (oxydehydrogenation) of the process according to the invention glycolic esters of the general formula HO—CH$_2$—COOR are used in the form of a vapor.

In this formula, R is a hydrocarbon radical, preferably an aliphatic, straight-chain or branched alkyl radical having 1 to 8 carbon atoms, in particular having 1 to 5 carbon atoms.

The gaseous glycolic esters are passed together with oxygen or an oxygen-containing gas, such as air, over the catalyst. It is preferable to dilute with a carrier gas, such as nitrogen or noble gases.

In the process according to the invention, in general the following amounts of additives are used for each mol of glycolic ester:
 Oxygen: 0.1 to 5 mol, preferably 0.5 to 3 mol.
 Carrier gas: 0 to 200 mol, preferably 30 to 100 mol.
 Satisfactory results are also obtained outside these limits.

In principle, all oxydehydrogenation catalysts are suitable as catalysts for the process according to the invention. However, the catalyst preferably contains at least one of the elements V, Au, Mo, Ag, Cu, Sn, Sb, Bi and P. Nevertheless, other elements of the 3rd to 5th main groups also exhibit a catalytic effect.

The specified elements are introduced into the reaction zone either in metallic form or in the form of their compounds, for example as oxides, nitrates, acetates, acetylacetonates, oxalates, citrates or halides.

It has proved to be advantageous to pass, before the introduction of the glycolic ester into the reaction zone, an oxidizing gas, in particular oxygen or air, or a reducing gas, in particular hydrogen or hydrogen which has been diluted with inert gas, over the catalyst at temperatures of 100° to 800° C., in particular 300° to 600° C.

The catalytically active elements are preferably applied to support materials. Particularly suitable supports are silicates, aluminas, aluminum silicates, pumice, silicon carbide or carbons. Silicates, aluminas or aluminum silicates are preferably used. Aluminum silicates with a BET surface area of less than 50 m$^2$/g are particularly advantageous.

The total amount of elements on the support can vary within wide limits. In general, it is 0.01 to 50% by weight, preferably 0.1 to 20% by weight, relative to the total mass of the supported catalyst. The catalytically active components are advantageously applied in the form of a solution onto the support, and then the solvent is evaporated off and the catalyst is dried. The solvents which are generally used are water, hydrochloric acid, nitric acid, alkali metal hydroxide solutions or aqueous ammonia solution, preferably water or hydrochloric acid.

However, it is also possible to use the active components without a support.

The oxydehydrogenation is generally carried out at temperatures between 100° and 600° C., preferably between 200° and 400° C. The holdup time (residence time) is preferably between 0.05 and 10 seconds, but is in particular between 0.05 and 1 second. Satisfactory results are also obtained outside these limits.

The oxydehydrogenation is preferably carried out under atmospheric pressure, but it is also possible to use reduced or elevated pressures, i.e. 0.01 to 100 bar.

The specific procedure of the oxydehydrogenation is such that the glycolic ester and oxygen, or an oxygen-containing gas, and, where appropriate, a carrier gas, are passed from metering devices into a vaporization zone, and the resulting gas mixture is then passed through a reaction tube which is heated externally and is packed with the catalyst. It has proved advantageous in this procedure to heat the oxygen, or the oxygen-containing gas, and the carrier gas to the reaction temperature before the introduction into the vaporization zone.

In the second stage of the process according to the invention, the gaseous reaction mixture from the oxydehydrogenation is, after leaving the reaction tube, passed together with an excess of an alcohol which is suitable as a water-entraining agent into a distillation column. Water is azeotropically removed overhead with a part of the excess alcohol and together with other low-boilers, for example formaldehyde and methyl formate. The bottom product is essentially composed of the desired glyoxylic hemiacetal ester, the remainder of the excess alcohol, small amounts of the alcohol derived from the ester group, and unreacted glycolic ester. The desired glyoxylic hemiacetal ester can be isolated by, for example, customary distillation.

It is preferable for the water to be completely removed overhead in order to avoid undesired hydrolysis reactions in the bottom product. The alcohol which has distilled over with the water can be obtained from the head product by known methods, for example distillation or phase separation, and can be recycled.

It is known that, in acid medium, the hemiacetals can react further with alcohols to give full acetals. In addition, it was to be expected that the introduction of a glyoxylic ester into an excess of alcohol under acid conditions would lead to transesterification reactions. Although small amounts of formic acid are present as a by-product in the reaction mixture, in other words acid conditions prevail, surprisingly only small amounts of these undesired by-products are formed in the process according to the invention.

However, not all aliphatic alcohols form azeotropes with water, one exception being, for example, methanol. In these cases, an additional inert entraining agent is used.

In addition, the majority of alcohols form an azeotrope which has a relatively high boiling point, namely 90° to 100° C. However, since many glyoxylic hemiacetal esters start to decompose above 90° C., when alcohols of this type are used for the acetalization it is advisable to use as the water-entraining agent an additional substance whose azeotrope boils below 90° C. This additional entraining agent should not undergo any undesired side reactions with the reaction mixture, in other words should be inert. In addition, it should be chosen such that its azeotrope is lower boiling than the alcohol used for the acetalization. (In the case mentioned previously, in which the alcohol itself is used as the entraining agent, its azeotrope is likewise lower boiling than the alcohol itself.) When alcohols such as ethanol, isopropanol and tert.-butanol are used for the acetalization, in general the alcohol will also be used as the entraining agent, since the corresponding azeotropes boil below 90° C. In such instances, although it is also possible to use an additional inert entraining agent, this signifies redundant effort.

Accordingly, the present invention also relates to a process for the preparation of glyoxylic hemiacetal esters, which comprises catalytic oxydehydrogenation of glycolic esters in the gas phase to give glyoxylic esters, and then reaction of the latter with an alcohol, the gaseous reaction mixture formed in the oxydehydrogenation being introduced, together with an excess of alcohol and an inert entraining agent whose azeotrope with water boils below 90° C. and below the alcohol which is used, into a distillation column and then distilling overhead the water of reaction together with other low-boilers and the entraining agent, the glyoxylic hemiacetal ester and the excess low-boilers and the entraining agents, the glyoxylic hemiacetal and the excess alcohol resulting as the bottom product.

An inert entraining agent whose azeotrope with water boils below 80° C. and below the alcohol which is used is preferably employed.

When an inert entraining agent forms a binary azeotrope with water, in general there is also formation of a ternary azeotrope of water, the alcohol which is used, and the entraining agent, so that some of the alcohol also distils overhead.

The entraining agent and the alcohol can be obtained from the head product by known methods, for example by distillation or by phase separation, and they can be recycled.

Alcohols which are suitable in principle for the preparation of the hemiacetal are all straight-chain or branched aliphatic alcohols having 1 to 8 carbon atoms. Saturated primary and secondary alcohols having 1 to 8 carbon atoms are preferred. Methanol, ethanol, n-propanol and n-butanol are particularly preferred.

In the process according to the invention, in general 1–30 mol of alcohol are used for each mol of glyoxylic ester. If the alcohol is also used as the entraining agent, then the amount of alcohol is preferably 2–20 mol per mol of ester. When an additional inert entraining agent is used, the amount of alcohol is preferably 2–10 mol per mol of ester.

Suitable inert entraining agents are derived from the series of aliphatic and aromatic hydrocarbons, which may contain heteroatoms, such as $CH_2Cl_2$, $CHCl_3$, $CCl_4$, n-pentane, n-hexane, cyclohexane and benzene. Obviously, the amount of entraining agent must be enough to remove the water of reaction overhead.

The gaseous mixture from the oxydehydrogenation reactor is generally introduced into one of the two lower thirds of the distillation column (including the bottom), preferably into the lowest third (including the bottom). The alcohol is generally introduced into the column above this stream of gas. The same applies to the inert entraining agent in the case where one is used.

Because of their high reactivity, glyoxylic esters and their hemiacetals are valuable starting materials and intermediates for a number of syntheses of pharmaceutically active compounds such as, for example, allantoin, substituted glycine or alkaloids (such as, for example, tetrahydroisoquinoline alkaloids).

The examples which follow are intended to illustrate the invention in detail.

EXAMPLE 1

The oxydehydrogenation of methyl glycolate was carried out at 320° C. using 22.5 ml of the catalyst described in Example 1 of U.S. Pat. No. 4,340,748. The amounts of the main components in the discharge from the reactor which were produced each hour are shown in Table 1:

TABLE 1

| Gas phase constituents | mmol/hour |
|---|---|
| Methyl glyoxylate | 112.0 |
| Methyl glycolate | 2.6 |
| Water | 123.2 |
| Methanol | 7.8 |
| Nitrogen | 6430.0 |
| Formic acid | 2.4 |

The discharge from the reactor also contained, for example, $O_2$, $CO$, $CO_2$, $HCHO$ and $HCOOCH_3$. The yield of methyl glyoxylate and the conversion were 86 and 98% respectively.

The gaseous discharge from the reactor was continuously introduced, together with a mixture of methanol and chloroform, into the bottom of a distillation column (length: 300 mm, diameter: 12 mm, packing: Braunschweiger helices). The amounts of methanol and chloroform introduced each hour were 30 g and 150 g respectively. The bottom contents were vigorously stirred, and the bottom temperature was 30° C. The action of the powerful stream of gas ensured the ready volatility of the bottom components. A mixture of chloroform, methanol, water and other low-boilers was removed overhead. During the experiment there was continuous discharge of part of the bottom mixture. After the experiment had lasted 4 hours, the remaining bottom contents were added to the bottom product which had already been discharged. This collected bottom mixture contained the following products:

| | |
|---|---|
| HO\CHCOOCH$_3$/CH$_3$O | 444.2 mmol |
| CH$_3$O\CHCOOCH$_3$/CH$_3$O | undetectable |
| HOCH$_2$COOCH$_3$ | 10.1 mmol |
| HO\CHCOOCH$_3$/CH$_3$OOCCH$_2$O | traces |
| Methyl glyoxylate | 2.7 mmol |
| H$_2$O | 22.3 mmol |

The glyoxylic ester and its hemiacetal were determined by $^{13}$C-NMR spectroscopy. Gas-chromatographic analytical methods were also used.

Thus, the methyl glyoxylate was almost quantitatively converted into the methyl hemiacetal, while 95.5% of the water of reaction was removed overhead.

EXAMPLE 2

The oxydehydrogenation conditions and composition of the gas phase were as in Example 1. The gaseous discharge from the reactor was introduced together with a mixture of 2-butanol (60 g/h) and n-hexane (100 g/h) into the bottom of the column. The temperature in the vigorously stirred bottom was 35° C. A mixture of 2-butanol, n-hexane, water and other low-boilers was removed overhead, and there was continuous discharge of part of the bottom mixture. After the experiment had lasted four hours, the collected bottom mixture contained the following products (R'=sec.-butyl):

| | |
|---|---|
| HO\CHCOOCH$_3$/R'O | 43.2 mmol |
| R'O\CHCOOCH$_3$/R'O | undetectable |
| HO\CHCOOR'/R'O | undetectable |
| HO\CHCOOCH$_3$/CH$_3$O | 13.2 mmol |
| HOCH$_2$COOCH$_3$ | 5.1 mmol |
| Methyl glyoxylate | undetectable |
| H$_2$O | 24.8 mmol |

Thus, full acetals and products of transesterification were unetectable.

EXAMPLE 3

The oxydehydrogenation conditions and composition of the gas phase were as in Example 1. The gaseous discharge from the reactor was passed together with ethanol (88 g/h) into the bottom of the column. In this case, ethanol served as reactant and entraining agent. The temperature in the vigorously stirred bottom was 58° C. A mixture of ethanol, water and other low-boilers was removed overhead, and there was continuous discharge of part of the bottom mixture. After the experiment had lasted four hours, the collected bottom mixture contained the following products:

| | |
|---|---|
| HO\CHCOOCH$_3$/C$_2$H$_5$O | 418.1 mmol |
| C$_2$H$_5$O\CHCOOCH$_3$/C$_2$H$_5$O | undetectable |
| HO\CHCOOC$_2$H$_5$/C$_2$H$_5$O | 16.3 mmol |
| HO\CHCOOCH$_3$/CH$_3$O | 7.2 mmol |
| HOCH$_2$COOCH$_3$ | 4.6 mmol |
| Methyl glyoxylate | 2.3 mmol |
| H$_2$O | 21.4 mmol |

EXAMPLE 4

The oxydehydrogenation conditions and composition of the gas phase were as in Example 1. The gaseous discharge from the reactor was introduced together with a mixture of n-octanol (73 g/h) and cyclohexane (50 g/h) into the bottom of the column. The temperature in the vigorously stirred bottom was 61° C. A mixture of n-octanol, water, cyclohexane and other low-boilers was removed overhead, and there was continuous discharge of a part of the bottom mixture. After the experiment had lasted four hours, the collected bottom mixture contained the following products:

| with R' = n-octyl | |
|---|---|
| HO\CHCOOCH₃/R'O | 439.5 mmol |
| R'O\CHCOOCH₃/R'O | undetectable |
| CH₃O\CHCOOCH₃/HO | traces |
| HO\CHCOOR'/R'O | undetectable |
| HOCH₂COOCH₃ | 7.8 mmol |
| Methyl glyxoylate | 6.1 mmol |
| H₂O | 16.7 mmol |

We claim:

1. A process for the preparation of a glyoxylic hemiacetal ester, which comprises catalytically oxydehydrogenating a glycolic ester in a gas phase at a temperature between 100° and 600° C. and a residence time between 0.05 and 1 second to give a gaseous reaction mixture containing a glyoxylic ester, introducing the gaseous reaction mixture with 1 to 30 mole of a saturated primary or secondary alcohol per mole of the glyoxylic ester into a distillation column, said alcohol having 2 to 8 carbon atoms and being suitable as an entraining agent, and then reacting the glyoxylic ester with the alcohol and distilling overhead the water of reaction, other low boilers and part of the excess alcohol to yield a glyoxylic hemiacetal ester and the remainder of the excess alcohol as the bottom product.

2. The process as claimed in claim 1, wherein the catalyst for the oxydehydrogenation contains at least one element selected from the group consisting of Ag, V, Mo, Cu, Au, Sn, Sb, Bi and P on a support.

3. The process as claimed in claim 1, wherein 2 to 20 mole of the alcohol per mole of the glyoxylic ester is introduced into the distillation column.

4. A process for the preparation of a glyoxylic hemiacetal ester, which comprises catalytically oxydehydrogenating a glycolic ester in a gas phase at a temperature between 100° and 600° C. and a residence time between 0.05 and 1 second to give a gaseous reaction mixture containing a glyoxylic ester, introducing the gaseous reaction mixture with an inert entraining agent and 1 to 30 mole of a saturated primary or secondary alcohol per mole of the glyoxylic ester into a distillation column, said alcohol having 1 to 8 carbon atoms and said inert entraining agent forming an azeotrope with water which boils below 90° C. and below the alcohol, and then reacting the glyoxylic ester with the alcohol and distilling overhead the water of reaction, other low boilers and the entraining agent to yield a glyoxylic hemiacetal ester and the excess alcohol as the bottom product.

5. The process as claimed in claim 4, wherein the catalyst for the oxydehydrogenation contains at least one element selected from the group consisting of Ag, V, Mo, Cu, Au, Sn, Sb, Bi and P on a support.

6. The process as claimed in claim 4, wherein the inert entraining agent is selected from the group consisting of CH₂Cl₂, CHCl₃, CCl₄, n-pentane, n-hexane, cyclohexane and benzene.

7. The process as claimed in claim 4, wherein 2 to 10 mole of the alcohol per mole of the glyoxylic ester is introduced into the distillation column.

8. The process as claimed in claim 4, wherein the inert entraining agent forms an azeotrope with water which boils below 80° C. and below the alcohol.

* * * * *